(12) United States Patent
Petit

(10) Patent No.: US 12,121,703 B2
(45) Date of Patent: Oct. 22, 2024

(54) FLUID INJECTION DEVICE

(71) Applicant: APTAR FRANCE SAS, Le Neubourg (FR)

(72) Inventor: Ludovic Petit, Vitot (FR)

(73) Assignee: APTAR FRANCE SAS, Le Neubourg (FR)

( * ) Notice: Subject to any disclaimer, the term of this patent is extended or adjusted under 35 U.S.C. 154(b) by 641 days.

(21) Appl. No.: 17/108,693

(22) Filed: Dec. 1, 2020

(65) Prior Publication Data
US 2021/0162130 A1 Jun. 3, 2021

(30) Foreign Application Priority Data
Dec. 2, 2019 (FR) ........................................ 1913622

(51) Int. Cl.
*A61M 5/20* (2006.01)
*A61M 5/315* (2006.01)
*A61M 5/32* (2006.01)

(52) U.S. Cl.
CPC ...... *A61M 5/2033* (2013.01); *A61M 5/31501* (2013.01); *A61M 5/31511* (2013.01); *A61M 5/3158* (2013.01); *A61M 5/32* (2013.01)

(58) Field of Classification Search
CPC ............ A61M 5/2033; A61M 5/31501; A61M 5/31511; A61M 5/3158; A61M 5/32;
(Continued)

(56) References Cited

U.S. PATENT DOCUMENTS 7,101,351 B2 * 9/2006 Crawford .............. A61M 5/326
604/110
2006/0178644 A1 * 8/2006 Reynolds .............. A61J 1/2093
604/232

(Continued)

FOREIGN PATENT DOCUMENTS

EP 2 489 385 A1 8/2012
WO 2009/114542 A1 9/2009
(Continued)

OTHER PUBLICATIONS

French Search Report for corresponding FR 1913622, dated Jul. 7, 2020.

*Primary Examiner* — Michael J Tsai
*Assistant Examiner* — Nidah Hussain
(74) *Attorney, Agent, or Firm* — Sughrue Mion, PLLC

(57) ABSTRACT

A fluid injection device including a syringe with a body (1), a piston (3), and a needle (2) with an injection tip (20); a piston rod (5); and a sleeve (10) around the syringe and axially movable between a non-projecting position in which said sleeve (10) does not cover the injection tip (20) and a projecting position. The sleeve (10) urged, while in said non-projecting position, towards its projecting position by a spring (30). The sleeve (10) has an inner portion (11) extending inside the body, and an outer portion (12) extending outside the body (1), the inner portion (11) including a radially-deformable tab (110) snap-fastened in a window (6) of the body (1), blocking the sleeve in its non-projecting position. A hollow member (40) co-operates, after injection, with the radially-deformable tab (110), so that after the fluid is injected, the sleeve is moved automatically towards its projecting position.

5 Claims, 1 Drawing Sheet

(58) Field of Classification Search
CPC ........ A61M 5/3243; A61M 2005/3261; A61M 2005/3265; A61M 2005/3252; A61M 5/3245; A61M 5/3257–3272; A61M 2005/3247
USPC ........................................................ 604/134
See application file for complete search history.

(56) References Cited

U.S. PATENT DOCUMENTS

| | | |
|---|---|---|
| 2008/0051715 A1 | 2/2008 | Young et al. |
| 2008/0097337 A1* | 4/2008 | Judd ..................... A61M 5/326 604/220 |
| 2015/0273161 A1* | 10/2015 | Bengtsson .......... A61M 5/3286 604/198 |
| 2018/0161507 A1* | 6/2018 | Fabien ................ A61M 5/3157 |

FOREIGN PATENT DOCUMENTS

| | | |
|---|---|---|
| WO | 2011/157930 A1 | 12/2011 |
| WO | 2016/174249 A1 | 11/2016 |

* cited by examiner

FLUID INJECTION DEVICE

The present invention relates to a fluid injection device, and more particularly to such a device provided with a safety device.

Safety devices for injection syringes, in particular syringes of the pre-filled type, are well known. Document FR 2 922 112 describes an example of such a prior-art device.

Such safety devices generally comprise an outer sleeve that is assembled around the syringe, and that is adapted to be deployed at the end of injection so as to cover the needle. Such devices may be complex to manufacture and to assemble, and their reliability is not always as good as it should be.

An object of the present invention is to provide an injection device that does not have the above-mentioned drawbacks.

Another object of the present invention is to provide an injection device that is reliable in use, that is safe, and that prevents any risk of injury.

Another object of the present invention is to provide an injection device that is simple and inexpensive to manufacture and to assemble.

The present invention thus provides a fluid injection device comprising:
- a syringe comprising a body defining a reservoir containing the fluid to be injected, a piston that is arranged to move axially in said body, and a needle provided with an injection tip that is fastened to said body;
- a piston rod that is axially movable relative to said body and that co-operates with said piston so as to move it axially in said reservoir; and
- a sleeve that is arranged around said syringe so as to be axially movable relative to said body between a non-projecting position in which said sleeve does not cover said injection tip, and a projecting position in which said sleeve covers said injection tip, said sleeve being in its non-projecting position before the injection device is actuated, and being urged, while in said non-projecting position, towards its projecting position by a compressed spring;
- said sleeve comprising an inner portion that extends, at least in part, inside said body, and an outer portion that extends outside said body, said inner portion including at least one radially-deformable tab that, in the non-projecting position of said sleeve, is snap-fastened in at least one respective window of said body, said snap-fastening blocking said sleeve in its non-projecting position, said device including a hollow member that co-operates, after injection, with said at least one radially-deformable tab so as to deform it radially inwards, thereby causing it to cease co-operating with its respective window of said body, so that after said fluid has been injected, said sleeve is moved automatically by said spring towards its projecting position.

Advantageously, a second piston is arranged to move axially in the body, said fluid to be injected being arranged between said piston and said second piston.

Advantageously, said second piston is perforated by said needle at the start of actuation.

Advantageously, said hollow member is of shape that is conical, and co-operates with said second piston.

Advantageously, said spring co-operates firstly with said outer portion of said sleeve, and secondly with a portion of said body of the syringe, in particular a radial projection.

Advantageously, said piston rod includes an outer bead that, at the end of actuation, co-operates with an inner radial recess of said body, so as to lock the device in the projecting position of said sleeve.

These and other characteristics and advantages of the present invention appear more clearly from the following detailed description, given by way of non-limiting examples, and with reference to the accompanying drawings, and in which.

Figure 1:
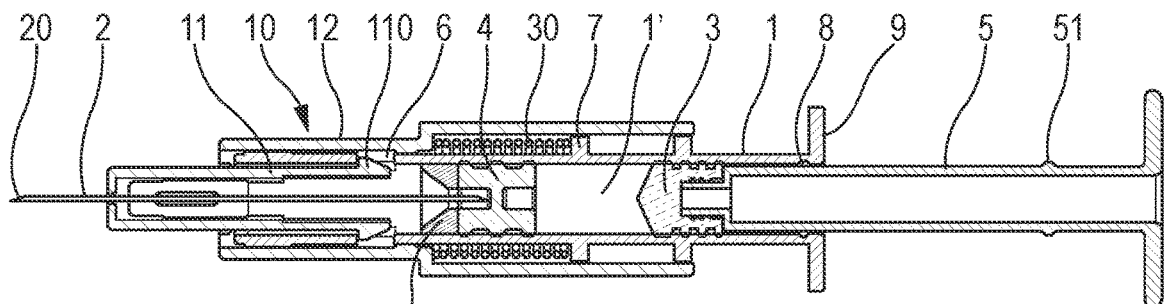
FIG. 1 is a diagrammatic section view of an injection device in an advantageous embodiment, in its position before injection.

The terms "proximal" and "distal" are relative to the needle. The terms "axial" and "radial" are relative to the longitudinal central axis of the device.

The manual injection device shown in the figures includes a syringe comprising a body 1 defining a reservoir 1' containing the fluid to be injected, a needle 2 that is fastened to said body 1 and through which the fluid is dispensed, and a piston 3 that is adapted to be moved in said body 1 so as to perform the injection.

The needle 2 includes an injection tip 20 that is jabbed into the injection zone during use.

A piston rod 5 co-operates with said piston 3 during injection so as to move it in the body 1.

In its proximal portion, the body 1 of the syringe includes at least one and preferably two windows 6 and a radial projection 7 that extends radially outwards, having functions that are described in detail below. Preferably at its distal end, the body 1 may be provided in conventional manner with a radial collar 9 against which the user can bear when actuating the piston rod 5. Advantageously, the body 1 further includes an inner radial recess 8, preferably in the proximity of said radial collar 9, and having a function that is also described in detail below.

Advantageously, a second piston 4 is provided in the body 1, the fluid to be dispensed being arranged between the piston 3 and the second piston 4. The function of the second piston 4 is to isolate the fluid before use, and it is perforated by the needle 2 at the start of actuation. The second piston 4 is also axially movable in said body 1 during actuation. The presence of the second piston guarantees the integrity of the fluid until actuation.

A sleeve 10 is provided around the syringe, being axially movable relative to the syringe between a non-projecting position and a projecting position. The sleeve 10 comprises an inner portion 11 that extends, at least in part, inside the body 1, and an outer portion 12 that extends outside the body 1.

Before injection, the sleeve 10 is arranged in its non-projecting position, in such a manner as to expose the injection tip 20 of the needle 2.

It should be observed that before use, the injection tip 20 may possibly be protected by an appropriate cap (not shown) that the user removes when it is desired to use the injection device. However, such a cap is not essential in the event that, prior to actuation, the fluid is isolated between two pistons 3, 4, as in the embodiment shown in the drawing.

After injection, said sleeve 10 is moved axially relative to the body 1 towards its projecting position in which it is arranged around the injection tip 20 of the needle 2, so as to avoid any risk of injury with said needle 2, thereby forming a post-injection safety device.

The outer portion 12 contains a spring 30 that co-operates firstly with said sleeve 10, and secondly with a portion of the body 1 of the syringe, in particular the radial projection 7 that is provided for this purpose. In the non-projecting position of the sleeve 10, the spring 30 is compressed, thereby urging said sleeve 10 axially towards its projecting position.

The inner portion 11 includes at least one and preferably two radially-deformable tabs 110 that, in the non-projecting position of the sleeve 10, are each snap-fastened in a respective window 6 of the body 1 of the syringe. Such snap-fastening prevents the sleeve 10 from being moved towards its projecting position, despite the force of the spring 30, and thus blocks said sleeve 10 in its non-projecting position.

At its proximal end, the second piston 4 is associated with a hollow member 40 that is advantageously conical, and that is adapted to co-operate, after injection, with said radially-deformable tabs 110 of the inner portion 11 of the sleeve 10.

Figure 2:
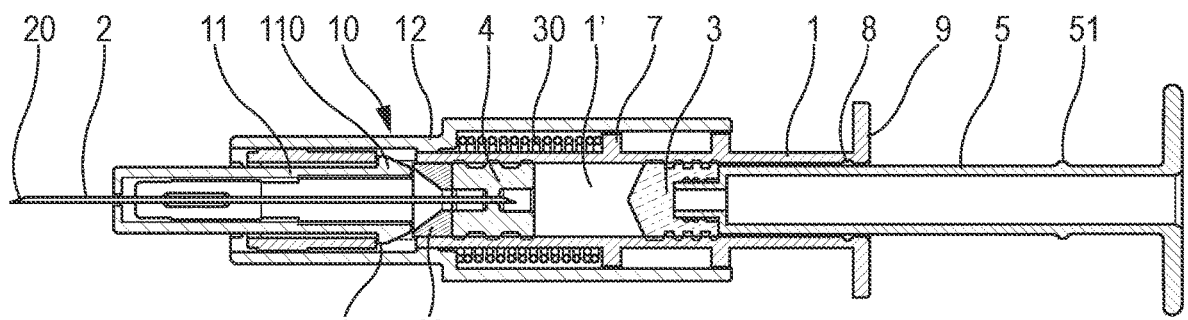
FIG. 2 is a view similar to the view in FIG. 1, during injection.

With reference to FIGS. 1 to 4, the user who wishes to use the injection device jabs the injection site with the injection tip 20 of the needle 2, and then exerts axial pressure on the piston rod 5. Said piston rod moves axially relative to the body 1, so as to move the piston 3 in the reservoir 1. This generates pressure in the fluid, and since the fluid is incompressible, it transmits the pressure to the second piston 4. The second piston is thus forced to move axially against the needle 2, which thus comes to perforate it, as can be seen in FIG. 2. From that moment on, axial movement of the piston rod 5 moves the piston 3 in the body 1, thereby expelling the fluid contained in the reservoir 1' through the needle 2 so as to inject it into the injection site.

Figure 3:
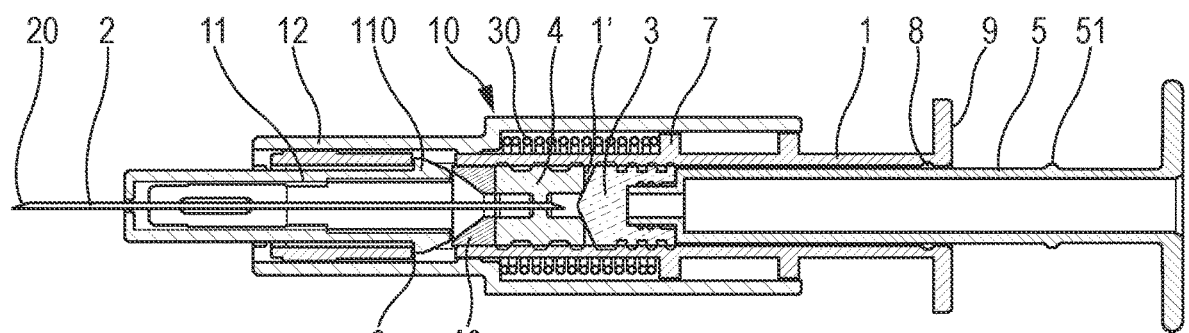
FIG. 3 is a view similar to the view in FIG. 2, at the end of injection, before the safety device has been triggered.
Figure 4:
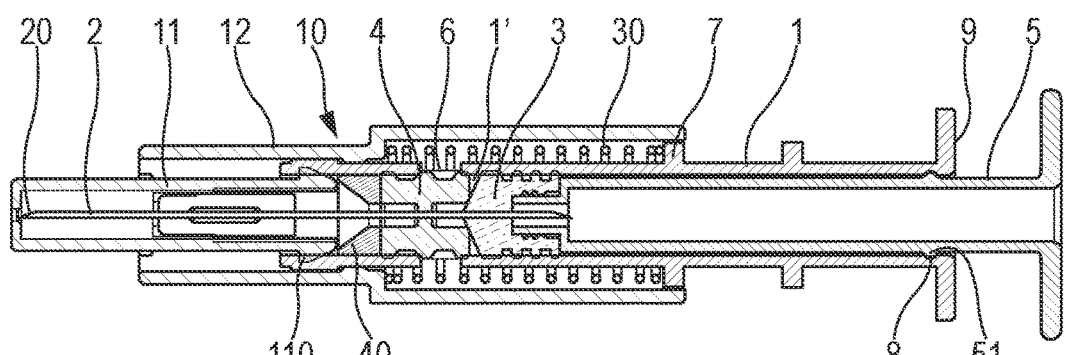
FIG. 4 is a view similar to the view in FIG. 3, after the safety device has been triggered.

At the end of injection, the piston 3 arrives in abutment against the second piston 4, itself in abutment against the hollow member 40, itself in contact with the inner portion 11 of the sleeve 10, as can be seen in FIG. 3. If the user continues to press axially on the piston rod 5, the hollow member 40 deforms the radially-deformable tabs 110 inwards, thereby causing them to cease co-operating with the windows 6 in the body 1, in particular to cease being snap-fastened therewith. Since the sleeve 10 is then no longer blocked, it is then moved automatically by the spring 30 towards its projecting position in which it covers the injection tip 20 of the needle 2, so as to avoid any risk of injury with the needle 2, as can be seen in FIG. 4.

The movement of the sleeve 10 towards its projecting position is thus triggered by a small axial movement of the piston rod 5, but thereafter it is independent of the user.

To finish off, the user moves the piston rod 5 manually towards a locked position in which an outer bead 51 on the piston rod 5 comes to co-operate with the inner radial recess 8 in the body 1, so as to lock the device with the sleeve 10 in its projecting position.

Optionally, in the rest position, the sleeve 10 could be connected to the syringe, e.g. by breakable bridges made by molding. The breakable bridges would then be broken at the end of injection, when the sleeve 10 is moved towards its projecting position. Thus, during the axial movement of the piston rod 5 relative to the reservoir 1, it is guaranteed that initially the fluid is injected through the needle 2, and that the sleeve 10 is moved only once injection has finished. The sleeve 10 may be connected to the syringe in the rest position in other ways, e.g. by friction or by mechanical jamming.

Although the present invention is described above with reference to an advantageous embodiment, naturally various modifications can be applied thereto by the person skilled in the art, without going beyond the ambit of the present invention, as defined by the accompanying claims.

The invention claimed is:

1. A fluid injection device comprising:
    a syringe comprising a body defining a reservoir containing the fluid to be injected, a piston that is arranged to move axially in said body, and a needle provided with an injection tip that is fastened to said body;
    a piston rod that is axially movable relative to said body and that co-operates with said piston so as to move it axially in said reservoir; and
    a sleeve that is arranged around said syringe so as to be axially movable relative to said body between a non-projecting position in which said sleeve does not cover said injection tip, and a projecting position in which said sleeve covers said injection tip, said sleeve being in its non-projecting position before the injection device is actuated, and being urged, while in said non-projecting position, towards its projecting position by a compressed spring;
    wherein said sleeve comprises an inner portion that extends, at least in part, inside said body, and an outer portion that extends outside said body said inner portion including at least one radially-deformable tab that, in the non-projecting position of said sleeve, is snap-fastened in at least one respective window of said body, said snap-fastening blocking said sleeve in its non-projecting position, said device including a hollow member that co-operates, after injection, with said at least one radially-deformable tab so as to deform it radially inwards, thereby causing it to cease co-operating with its respective window of said body, so that after said fluid has been injected, said sleeve is moved automatically by said spring towards its projection position; and wherein said spring co-operates firstly with said outer portion of said sleeve, and secondly with a radial projection of said body of the syringe.

2. The device according to claim 1, wherein a second piston is arranged to move axially in the body, said fluid to be injected being arranged between said piston and said second piston.

3. The device according to claim 2, wherein said second piston is perforated by said needle at the start of actuation.

4. The device according to claim 2, wherein said hollow member is of shape that is conical, and co-operates with said second piston.

5. The device according to claim 1, wherein said piston rod includes an outer bead that, at the end of actuation, co-operates with an inner radial recess of said body, so as to lock the device in the projecting position of said sleeve.

* * * * *